United States Patent
Yeakley et al.

(10) Patent No.: US 9,957,550 B2
(45) Date of Patent: May 1, 2018

(54) ATTENUATORS

(71) Applicant: BioSpyder Technologies, Inc., Rancho Santa Fe, CA (US)

(72) Inventors: Joanne M. Yeakley, Encinitas, CA (US); Bruce Seligmann, Tucson, AZ (US); Joel McComb, Rancho Santa Fe, CA (US)

(73) Assignee: BIOSPYDER TECHNOLOGIES, INC., Rancho Santa Fe, CA (US)

( * ) Notice: Subject to any disclaimer, the term of this patent is extended or adjusted under 35 U.S.C. 154(b) by 599 days.

(21) Appl. No.: 14/480,525

(22) Filed: Sep. 8, 2014

(65) Prior Publication Data

US 2016/0068886 A1   Mar. 10, 2016

(51) Int. Cl.
*C12Q 1/68*   (2018.01)

(52) U.S. Cl.
CPC ......... *C12Q 1/6806* (2013.01); *C12Q 1/6816* (2013.01); *C12Q 1/6841* (2013.01)

(58) Field of Classification Search
None
See application file for complete search history.

(56) References Cited

U.S. PATENT DOCUMENTS

| | | |
|---|---|---|
| 6,812,005 B2 | 11/2004 | Fan et al. |
| 7,361,488 B2 | 4/2008 | Fan et al. |
| 7,582,420 B2 | 9/2009 | Oliphant et al. |
| 8,150,627 B2 | 4/2012 | Fan et al. |
| 8,188,265 B2 | 5/2012 | Costa et al. |
| 8,288,103 B2 | 10/2012 | Oliphant et al. |
| 2004/0137484 A1 * | 7/2004 | Zhang et al. .......... C12Q 1/682 435/6.11 |
| 2011/0045462 A1 | 2/2011 | Fu et al. |
| 2012/0302451 A1 | 11/2012 | Fu |
| 2013/0244882 A1 | 9/2013 | Oliphant et al. |

OTHER PUBLICATIONS

Li et al., "Determination of tag density required for digital transcription analysis: Application to an androgen-sensitive prostate cancer model," PNAS, vol. 105, No. 51, pp. 20179-20184, Dec. 23, 2008.
Li et al., "Versatile pathway-centric approach based on high-throughput sequencing to anticancer drug discovery," PNAS, vol. 109, No. 12, pp. 4609-4614, Mar. 20, 2012.
Gerhold, "RASL-Seq: A Gene Expression Platform to Identify Toxicity Mechanisms and Adaptive Responses," National Center for Advancing Translational Sciences presentation slides, 19 pages, Mar. 20, 2014.
Wang et al., "Timing of plant immune responses by a central circadian regulator," Nature, vol. 470, pp. 110-115, Feb. 3, 2011.
Zhou et al., "The Akt-SRPK-SR Axis Constitutes a Major Pathway in Transducing EGF Signaling to Regulate Alternative Splicing in the Nucleus," Molecular Cell, vol. 47, pp. 422-433, Aug. 10, 2012.
"Attenuation Strategies for Highly Expressed Genes in the nCounter™ Gene Expression Assay," NanoString Technologies, 2009, 4 pages.
Lalonde, M.S., et al., "Sensitive Oligonucleotide Ligation Assay for Low-Level Detection of Nevirapine Resistance Mutations in Human Immunodeficiency Virus Type 1 Quasispecies,"J. Clin. Microbiol., vol. 45, No. 8, pp. 2604-2615, Aug. 2007.
Larman, H.B., et al., "Sensitive, multiplex and direct quantification of RNA sequences using a modified RASL assay," Nucleic Acids Research, vol. 42, No. 14, pp. 1-12, Jul. 25, 2014.
Li, H., et al., "RASL-seq for Massively Parallel and Quantitative Analysis of Gene Expression," Current Protocols in Mol. Biol., pp. 4.13.1-4.13.9, Apr. 2012.
"The Internal Normalizer: Making Conventional RT-PCR More Quantitative," Super Array Bioscience Corporation, retrieved from <www.sabiosciecnes.com/newsletter/internal.html> on Jul. 17, 2014.

* cited by examiner

*Primary Examiner* — Kaijiang Zhang
(74) *Attorney, Agent, or Firm* — Wilson Sonsini Goodrich & Rosati

(57) ABSTRACT

Methods for detecting nucleic acid sequences, where attenuator oligonucleotides are provided to reduce the number of detection products resulting from highly abundant sequences.

37 Claims, 6 Drawing Sheets

Fig. 5: Combinations of mutated attenuators upstream detectors:

| downstream detectors: | | wildtype p-GGA- | 2b_U p-GGt- | 1b_U p-GcA- | 0b_U p-cGA- | 5b_U p-Gct- | 3b_U p-cGt- | 6b_U p-ccA- | 4b_U p-cct- |
|---|---|---|---|---|---|---|---|---|---|
| wildtype | -CCA | 100.000% | 74.118% | 28.224% | 1.232% | 12.792% | 0.207% | 0.056% | 0.028% |
| 2b_D | -gCA | 61.590% | 33.058% | 9.710% | 0.363% | 3.137% | 0.023% | 0.000% | 0.000% |
| 1b_D | -CgA | 2.183% | 0.778% | 0.215% | 0.011% | 0.047% | 0.000% | 0.050% | 0.000% |
| 0b_D | -CCt | 0.844% | 0.229% | 0.082% | 7.299% | 0.008% | 0.803% | 0.075% | 0.007% |
| 5b_D | -ggA | 0.081% | 0.509% | 0.061% | 0.000% | 1.169% | 0.058% | 0.017% | 0.041% |
| 3b_D | -gCt | 0.221% | 0.139% | 0.013% | 1.423% | 0.000% | 0.201% | 0.005% | 0.005% |
| 6b_D | -Cgt | 0.009% | 0.000% | 0.000% | 0.010% | 0.000% | 0.000% | 0.000% | 0.000% |
| 4b_D | -ggt | 0.000% | 0.032% | 0.000% | 0.000% | 0.000% | 0.020% | 0.006% | 0.000% |

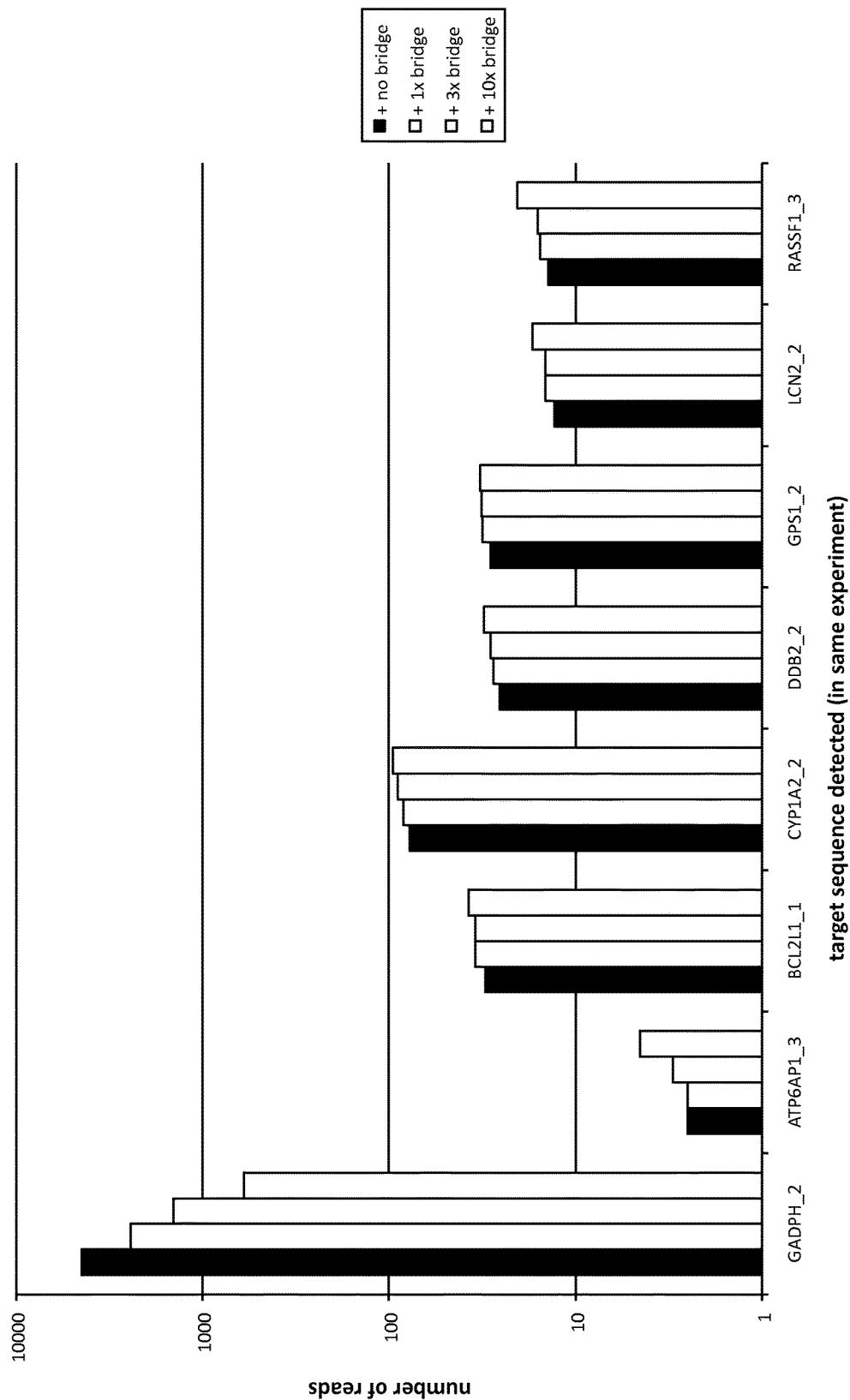

ATTENUATORS

STATEMENT OF GOVERNMENT SUPPORT

This invention was made with government support under grants 1R43HG007339-01 and 5R43HG007339-02 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 30, 2014, is named 42722701201_SL.txt and is 2,791 bytes in size.

BACKGROUND OF THE INVENTION

This invention relates to molecular biology, and more particularly to methods for detecting nucleic acid sequences where certain sequences in a sample are highly abundant.

BRIEF SUMMARY OF THE INVENTION

This invention provides methods for detecting target nucleic acid sequences of interest in a sample. In a typical ligation assay, the sample is contacted with a pool of detector oligonucleotides, where a pair of detector oligonucleotides is provided for each target sequence: a downstream detector (DD) and an upstream detector (UD). A downstream detector can have a portion (DR') that is complementary to a region of the target sequence designated as a downstream region (DR). An upstream detector can have a portion (UR') that is complementary to a region of the target sequence designated as the upstream region (UR).

The detectors are allowed to hybridize to nucleic acids in the sample. When downstream and upstream detectors both hybridize to the corresponding regions of the same target sequence, and the DR and UR are directly adjacent, the detector oligos can be ligated. Where the DR and UR are separated by one or more nucleotides, the DR can be extended prior to ligation to the UR. Formation of a ligation product thus serves as evidence that the target sequence was present in the sample. In some assay formats, the ligation product can be amplified with primers (e.g. P1, P2) where the detector oligos have corresponding primer hybridization sequences (e.g. P1, P2'), or the complements thereof. The ligation product (or its amplicons) can be detected by methods such as labeling for detection on an array, qPCR, or sequencing.

Where certain target sequences may be highly abundant in a sample, however, it can be desirable to detect the presence of those highly abundant target sequences (HATs), while attenuating the overall number of HAT-related ligation or amplification products to be detected, in order to facilitate the detection of the other target sequences of interest in the sample. Accordingly, this invention provides attenuator oligonucleotides. Some attenuators are provided that can replace one or both detectors for a HAT. Other attenuators can be contacted with the sample in competition with the detectors. This invention also provides sets of attenuator oligonucleotides, which can be specific for cell or tissue types, and kits containing such attenuators.

BRIEF DESCRIPTION OF THE DRAWINGS

FIG. 5 shows the attenuated detection of the target sequence GAPDH_2 when using various combinations of mutated downstream attenuators and mutated upstream attenuators.

FIG. 6 shows the attenuated detection of GAPDH_2 using bridge attenuators, while showing the enhanced detection of selected less-abundant target sequences.

DETAILED DESCRIPTION OF THE INVENTION

Figure 1:
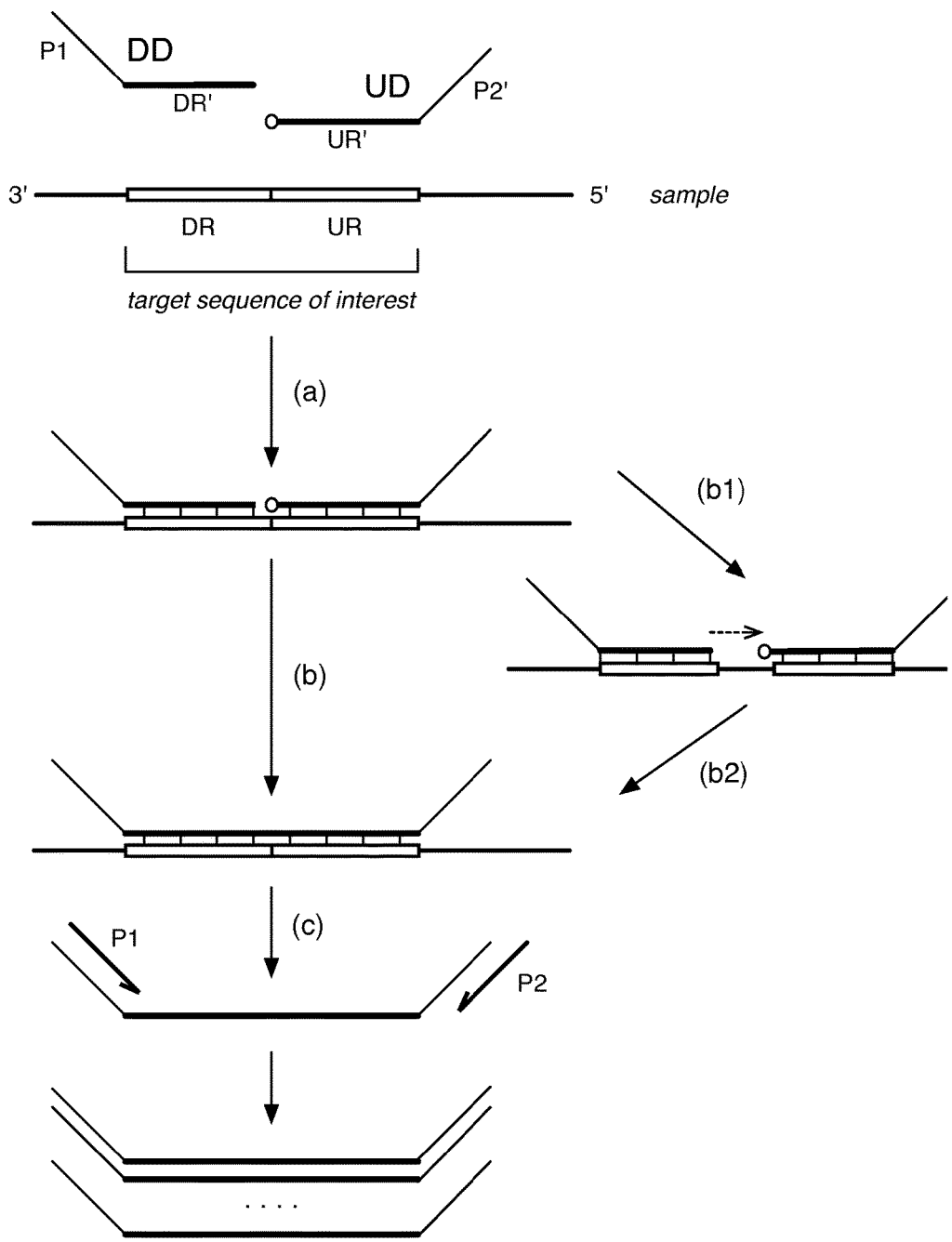
FIG. 1 illustrates a representative ligation assay for detection of target nucleic acid sequences.

This invention provides methods for detecting target nucleic acid sequences of interest in a sample. The sample can be any substance where it is desired to detect whether a target sequence of a nucleic acid is present. Such samples can be from living or dead organisms, or from artificially created or environmental samples. The samples can be in the form of tissue samples, cell samples, or samples that are cell-free. The samples can be provided in liquid phase, such as cell-free homogenates or liquid media from tissue cultures, or in solid phase, such as when the sample is mounted on a slide or in the form of formalin-fixed paraffin-embedded (FFPE) tissue or cells.

The target nucleic acid sequence of interest to be detected in a sample can be a sequence or a subsequence from DNA, such as nuclear or mitochondrial DNA, or cDNA that is reverse transcribed from RNA in the sample. The sequence of interest can also be from RNA, such as mRNA, rRNA, tRNA, miRNA, siRNAs, antisense RNAs, or long noncoding RNAs. More generally, the sequences of interest can be selected from any combination of sequences or subsequences in the genome or transcriptome of a species or an environment.

Highly Abundant Target Sequences of Interest (HATs)

In cases where there is more than one target sequence of interest in a given sample, it is likely that they will be present in different amounts. Moreover, the amount of a target sequence can vary among similar samples. Ideally, a detection assay will have sufficient dynamic range to measure the presence of the different target sequences quantitatively in a single experiment. For some types of samples, however, the range of abundance for various sequences of interest can span several orders of magnitude. For example, when profiling the RNA expression products of a cell, individual sequences of particular interest may be present in very few copies, while others are highly abundant target sequences (HATs). The HATs can be present in a sample in such large numbers that they may diminish the ability of a method to detect the presence of less abundant target sequences.

Depending on the cell or tissue type, such highly abundant HATs can include sequences encoding what are generally referred to as housekeeping genes. Examples of HATs include sequences that encode all or a portion of myoglobins, actins, tubulins, ubiquitins, heat-shock proteins (HSPs), ribosomal proteins, ribosomal RNAs (rRNAs), micro-RNAs (miRNAs), or small nuclear RNAs (snRNAs). Other examples of HATs can encode all or a portion of cytochrome c, glyceraldehyde 3-phosphate dehydrogenase (GAPDH), ribosomal protein L7 (RPL7), ribosomal protein S6 (rpS6), snRNA RNUs, phosphoglycerokinase (PGK), tyrosine 3-monooxygenase/tryptophan 5-monooxygenase activation protein zeta (YWHAZ), beta-actin, or beta-tubulin. Further examples include sequences encoding all or a portion of alpha-2-microglobulin, vimentin, and fibronectins. Yet other examples of HATs encode all or part of a cytochrome such as mitochondrially encoded cytochrome b (MT-CYB), outer mitochondrial membrane cytochrome b5 type B, microsomal cytochrome b5 type A (ACYB5A), and ascorbate-dependent cytochrome b3 (CYBASC3).

Because which sequences are highly abundant can differ from one sample type to another, such as between different tissues or cell types, certain target sequences can be designated as a predetermined set of potential HATs based on a search of the literature for that type of sample, or can be determined by performing preliminary assays to determine the more abundant sequences in the sample type. For some sample types, the number of HATs in a predetermined set can range in any combination of upper and lower limits of 1, 2, 5, 10, 20, 50, 100, 200, 500, 1000, 2000, 5000, and 10,000. For example, a useful predetermined set can have 1-10 HATs, 5-20 HATs, or 100-5000 HATs. Likewise, the number of HATs in a predetermined set can be expressed as a percentage of the total number of target sequences of interest, ranging in any combination of upper and lower limits of 0.1%, 0.2%, 0.5%, 1%, 2%, 5%, 10%, 20%, 25%, 30%, 35%, 40%, 45%, and 50%.

Ligation Assays

While many methods can be used to detect the presence of a target sequence, a representative method is a ligation assay, such as in Example 1 and illustrated schematically in FIG. 1. In a typical ligation assay, the sample is contacted with a pool of detector oligonucleotides ("detectors"). For each target sequence of interest, a pair of detectors is provided: a downstream detector (DD) and an upstream detector (UD). A downstream detector can have a portion (DR') that is complementary to a region of the target sequence designated as a downstream region (DR). An upstream oligo can have a portion (UR') that is complementary to a region of the target sequence designated as the upstream region (UR). Here, the terms "downstream" and "upstream" are used relative to the 5'-to-3' direction of transcription when the target sequence is an mRNA. The DR and UR of a target sequence are typically subsequences of the entire target sequence of interest, and an individual target sequence can have more than one set of DRs and URs, which can be selected by the user to optimize the performance of the assay. Multiple sets of DRs and URs can provide multiple measurements of the same target sequence or of different portions of the target sequence, such as different exons or exon junctions, or provide measurement of a portion of sequence that is not mutated versus a portion of sequence that may harbor a mutation. In some cases, the DR and UR are directly adjacent; in other cases, they can be separated by one or more nucleotide positions on the target sequence. In other cases, a portion of the DD can overlap with the UR sequence to which the UD hybridizes so that after hybridization of both the UD and the DD, there is an overhang sequence of 1, 2, 3, or more bases.

The DD or UD, or both, can contain a barcode sequence. For example, a useful barcode sequence can uniquely identify the specific gene or target sequence, or a group of select genes or target sequences within the sample that are being measured. Such sequences can be positioned between the UR' and P2' sequence, and/or between the DR' and P1 sequence, so they are amplified when using flanking primers.

In a ligation assay, the pool of detector oligos is contacted with the sample. As shown in FIG. 1, the DR' of the DD and the UR' of the UD for each target sequence are allowed to hybridize (a) to the corresponding DR and UR of the target sequence, if present in the sample, serving as a template.

When the DR and UR of a target sequence are directly adjacent, the detector oligos can be ligated (b): thus formation of a ligation product serves as evidence that the target sequence (DR+UR) was present in the sample. The ligation reaction can occur by chemical ligation or by using a ligase. A variety of nick-repairing ligases are commercially available to catalyze the formation of a phosphodiester bond between adjacent single-stranded polynucleotides when hybridized to another single-stranded template. An example is bacteriophage T4 DNA ligase, which uses ATP as a co-factor. The ATP can be supplied during the ligase reaction. In other reactions, the ligase can be pre-adenylated. In other reactions, the UD must be pre-adenylated at the 5' end, as with a 5' App DNA/RNA ligase. The UD in a typical reaction will have a 5'-phosphate to facilitate ligation to the DD, although this is not necessary, depending on the selection of ligase and ligation conditions. Where a 5'-phosphate on the DD is required for efficient ligation, using a comparable oligonucleotide without 5'-phosphorylation can be used to inhibit ligation.

In cases where DR and UR are separated by one or more nucleotide positions on the target sequence template, an extension step (b1) can be performed, as shown in FIG. 1, followed by the ligation step (b2). Ligation can also be preceded by a cleavage step, such as by a nuclease, to remove any overhangs. A useful enzyme is a Flap endonuclease (FEN), such as Fen-1.

Where the ligation assay proceeds directly to a detection step, either or both detectors can be designed to be labeled appropriately for detection. For example, the detector can be labeled with a color or fluorescent dye, latex bead, quantum dots, or nanodots. The label can also take the form of an additional nucleotide sequence that serves to enable detection and identification, such as a barcode sequence.

In some embodiments, the hybridization, ligation, or extension steps can be performed while the target sequence is in situ. This can be particularly useful, for example, when the sample is on histological slide, so that the ligation is known to occur at a recordable location and can be compared to similar reactions at other locations on the slide. In a particular embodiment, the ligation products can be eluted from the sample in situ for collection and further processing, preferably eluting from small areas to preserve the location information of the ligation reaction products.

In some assay formats, the ligation products can be (c) amplified to facilitate detection. As illustrated in FIG. 1, the detectors can have additional sequences ("tails") including primer hybridization sequences (e.g. P1, P2') or complements thereof, that serve as amplification sequences, so that after ligation, the ligation product can be amplified with a pair of amplification primers (P1, P2). An exemplary downstream amplification sequence (P1) is 5'-CAAGCA-GAAGACGGCATACGAG-3' (SEQ ID NO: 10), which can be used with a primer having the same sequence (P1). An exemplary upstream amplification sequence (P2') is 5'-ATCTCGGTGGTCGCCGTATCATT-3' (SEQ ID NO: 11), which can be used with primer P2 (shown in 3'-5' orientation): 3'-TAGAGCCACCAGCGGCATAGTAA-5' (SEQ ID NO: 12).

If desired, the amplification primer can incorporate a barcode sequence, for example a barcode sequence that uniquely identifies the sample in a multi-sample experiment.

The barcode sequence can be incorporated into the primer, such as 3' to the amplification sequence, so that the barcode becomes part of the amplified strand. In other instances, the amplification sequence of the primer can be extended by an additional sequence to provide a primer hybridization sequence that can be used for use in subsequent sequencing steps. The barcode may also be interposed between the amplification sequence, and if desired, the extended amplification sequence, and another sequence that can be used for capture, such as capture onto a surface as part of a sequencing process, and/or for yet another primer hybridization sequence that is used for sequencing. In each case the barcode will be amplified with the rest of the detector sequences, for instance forming a single amplified, elongated molecule that contains sequencing primer hybridization sequences, sample barcode, and a gene-specific sequence, which may include a gene-specific barcode as well as sequence or complement to the sequence of the target gene. In the case where the targeted oligo is a cDNA, a gene-specific sequence or a sample specific sequence can be added as part of the primer used for reverse transcription, and be a part of the sequence targeted by the UD and DD.

In other instances, methods known in the art can be used to amplify the ligated DD and UD sequences, such as by repetitive cycles of (1) ligation, (2) heating to melt off the ligated product, (3) cooling to permit hybridization of DD and UD to the target, (4) ligation, then repeating the heating (2), cooling (3), and ligation (4) steps. These additional amplification steps can be performed before amplification step (c), during which the sample barcodes and other sequences are added to the ligated UD and DD sequence. The target of the UD and DD hybridization may also be amplified by whole transcriptome amplification of RNA or amplification of cDNA.

The ligation product (or its amplicons) can then be detected by methods such as sequencing, qPCR, or labeling for detection on an array. Depending on the detection method, the skilled user will be able to modify the design of the detectors and amplification primers to include functional features that are appropriate, such as for bridge amplification on a sequencing flow cell.

Attenuators

In the context of the assays described above, this invention discloses various attenuator oligonucleotides ("attenuators") that can be used to attenuate the overall number of HAT-related ligation or amplification products to be detected. Some attenuators are provided that can replace one or both of the detectors for a HAT to provide positive detection of the HAT in the sample, but at a lower level of signal. These and other attenuators can also be added to the ligation reaction to attenuate the signal for the HATs. For purposes of discussion, the various attenuators can be also grouped as interacting with the detectors and target sequences at different stages of the assay. However, the Applicant does not wish to be bound by any proposed mechanisms of action as long as attenuation of detection is achieved.

Figure 2:
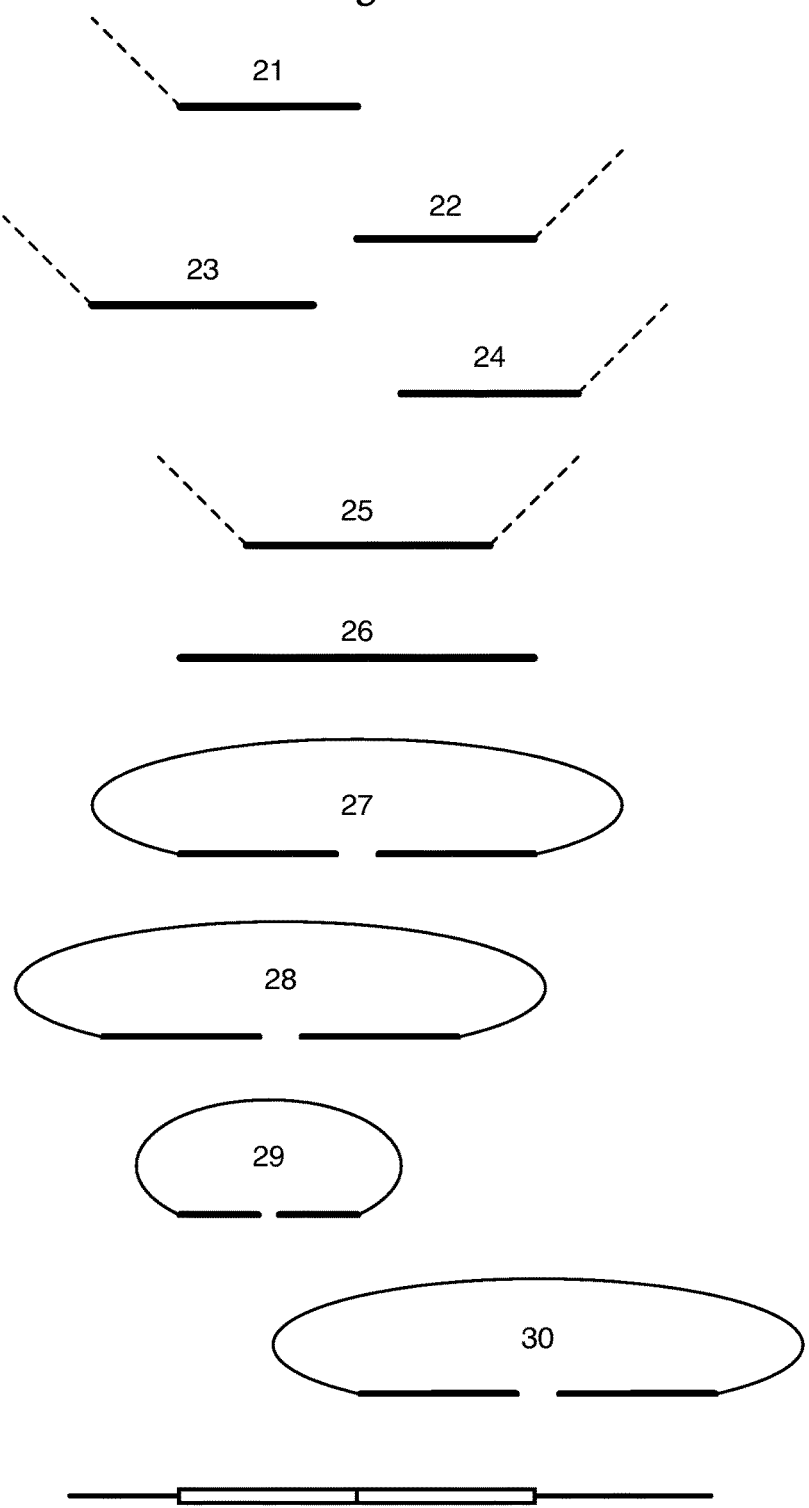
FIG. 2 depicts various oligonucleotides that attenuate primarily before and during hybridization. When an attenuator oligonucleotide is depicted with an optional sequence (sometimes a "tail"), this is depicted by a dotted line.

Attenuators can hybridize competitively with part or all of a DR and/or UR of a HAT. As shown in FIG. 2, attenuator 21 can hybridize to a portion of a DR, reducing access of a corresponding DD to the same DR. Similarly, attenuator 22 can hybridize competitively to a portion of an UR. An attenuator 23 or 24 can also have a portion that is complementary to regions of the HAT beyond the DR or UR. Because the length of such extended attenuators may be more comparable to the length of a DD or UD in the assay, their binding properties may be more thermodynamically similar to a DD or UD. Thus, the overall length of an attenuator, not just the ratio of a specific attenuator concentration to the DD or UD concentration in the hybridization cocktail, can be tuned to provide the desired level of attenuation for a particular HAT. As with all attenuators disclosed herein, the length and sequence of the oligonucleotide can be tuned for desired properties such as specificity, and annealing and melting temperatures. For example, an attenuator may be tuned to increase or decrease the number of C:G pairs formed during hybridization steps of the assay.

A bridge attenuator 25, which has portions that are complementary to subsequences of the DR or UR, may also compete effectively with both DDs and UDs for binding to the DR and UR. A full bridge attenuator 26 blocks the DR and UR of a HAT from hybridizing with either or both of a DD or UD, and its effectiveness is illustrated in Example 3.

A class of circularizing attenuator is provided that has hybridization sequences connected via a linking sequence so that when it hybridizes to a portion of the target sequence, it circularizes using the target sequence as a splint. For example in FIG. 2, attenuator 27 has a DR' and UR' connected by a flexible linker. The attenuator can also have various combinations of sequences that hybridize
- to at least part of the DR and the UR (as in 28, for example);
- to a portion of a DR, in addition to adjacent downstream sequence of the target sequence (as in 28);
- to a portion of an UR, in addition to adjacent upstream sequence of the target sequence;
- to two different portions of the DR (as in 29) or UR; and/or
- to a portion of either or both of the DR or UR with one end of the circularizing attenuator, and to a region of the sample that is separated by one or more nucleotides from the DR or the UR of the target sequence (as in 30);

as long as the hybridization of the circularizing attenuator reduces the number of UD or DDs hybridizing or ligating at the target sequence of a HAT. The 5' ends of the circularizing attenuators may be phosphorylated to facilitate ligation as appropriate to the ligation enzyme and conditions used.

As single molecules, these circularizing molecules can have superior hybridization characteristics compared to two separate attenuators having similar complementary regions. In contrast to a molecular inversion (padlock) probe, however, the oligonucleotide does not serve a detection function, but to attenuate the formation of HAT-related products to be detected.

Figure 3:
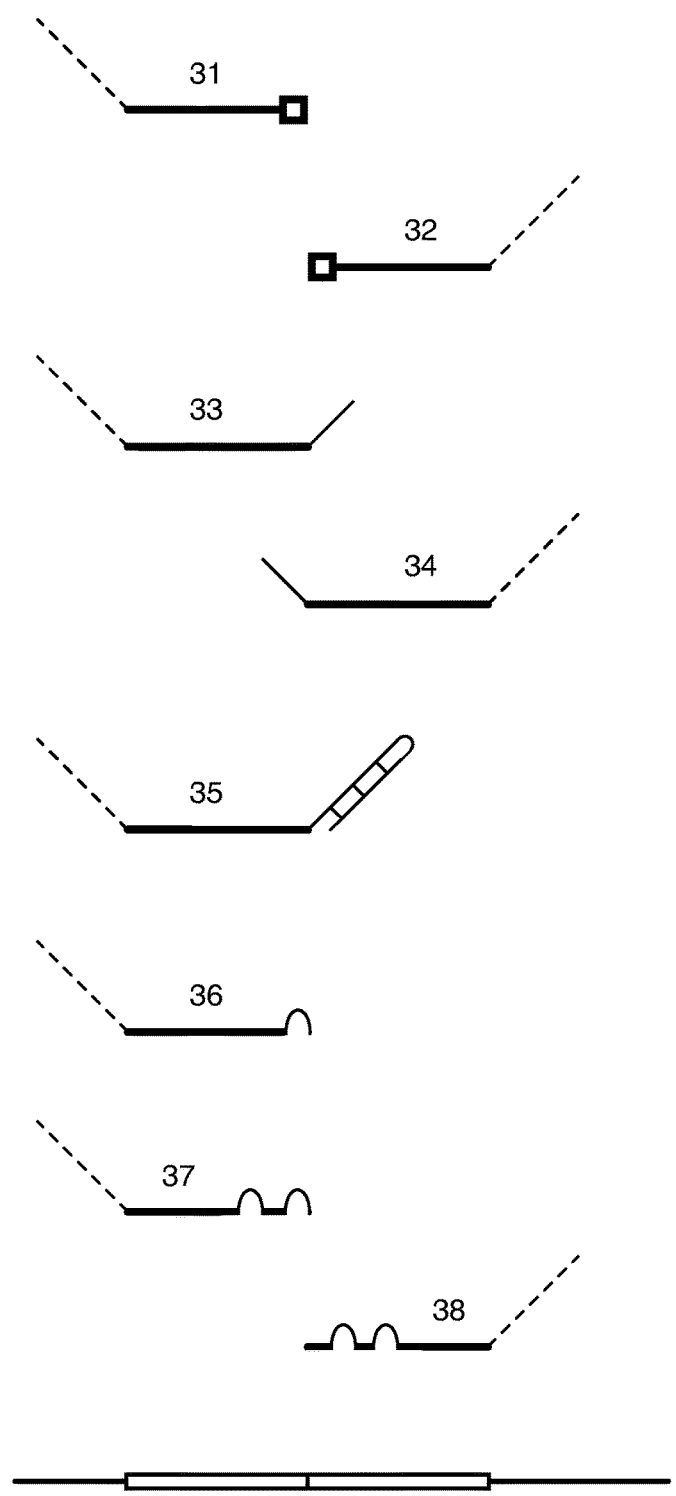
FIG. 3 depicts various oligonucleotides that attenuate primarily during ligation or extension.

Attenuators are provided that have a group that blocks effective ligation between a DD and an UD during the assay. For example, in FIG. 3, an attenuator 31 hybridized to a DR of a HAT can be similar to a DD, except having a blocking group at the 3' end to prevent ligation to an UD hybridized to the same HAT. Likewise, an attenuator 32 similar to an UD can be provided with a blocking group at the 5' end to prevent ligation between the DD and the attenuator. Useful blocking groups include nucleotides with modified bases (as discussed below) and spacer groups that prevent ligation with the ligase or chemical ligation method being used.

Examples of blocking groups at the 3' end for the UD include a 2',3'-dideoxynucleotide, 3'-propyl, 3'-dehydroxylation, 3'-amination, and an inverted (3'-3') linkage.

Examples of blocking groups at the 5' end for the DD include 5'-amination, 5'-adenylation, 5'-hexynyl, and an inverted (5'-5') linkage.

For ligases that require a double-stranded substrate, a ligation-blocking group can be a portion of nonhybridizing sequence. For example, an attenuator 33 that binds to a DR will present a single-stranded portion that will not ligate (or at least ligate at lower efficiency) than a comparable DD. Similarly, an attenuator 34 will ligate less efficiently, if at all, to a DD hybridized to the same HAT. Yet another attenuator 35 can have a nonhybridizing portion that forms a secondary structure, such as hairpin loop, to reduce ligation.

An embodiment of attenuator oligonucleotide that can replace a detector can have a portion partially complementary to the downstream or upstream region of the HAT. A particular embodiment is when the attenuator has a sequence similar to a detector, but has one or more mutated positions. Examples of such mutated attenuators are described in Example 2. Some mutated DDs have one (36), two (37, 38), or three mismatches (relative to the DR template) at positions at (36, 37) or near (38) the 3' end. Some mutated UDs have one, two, or three mismatches (relative to the UR template) at positions at or near the 5' end. A mutated DD can be used in combination with an unmutated ("wildtype") UD; a mutated UD can be used with a wildtype DD; or various mutated upstream and downstream detectors can be combined, depending on the degree of attenuation desired. Moreover, a mutated attenuator for a HAT can also be useful when provided during hybridization in addition to the wildtype detectors for the same HAT.

Another embodiment of attenuator reduces the number of ligation products to be detected by being more difficult to separate from the target sequence than comparable detectors. For example, attenuators may be designed to have higher melting temperatures so that fewer detectors are able to compete for the same target sequences. Attenuators can also be designed so that when hybridized to the target sequence with a detector or a second attenuator, the ligation product is more likely to remain hybridized to the target than the ligated pairs of detectors. This can be achieved by modifying the attenuator to cross-link to the target via oligo-directed cross-linking or by photo-activated cross-linking.

Yet another embodiment of an attenuator contains a modification or a segment that renders the attenuator or a ligation product more difficult or impossible to amplify when an amplification step is included in the assay.

Figure 4:
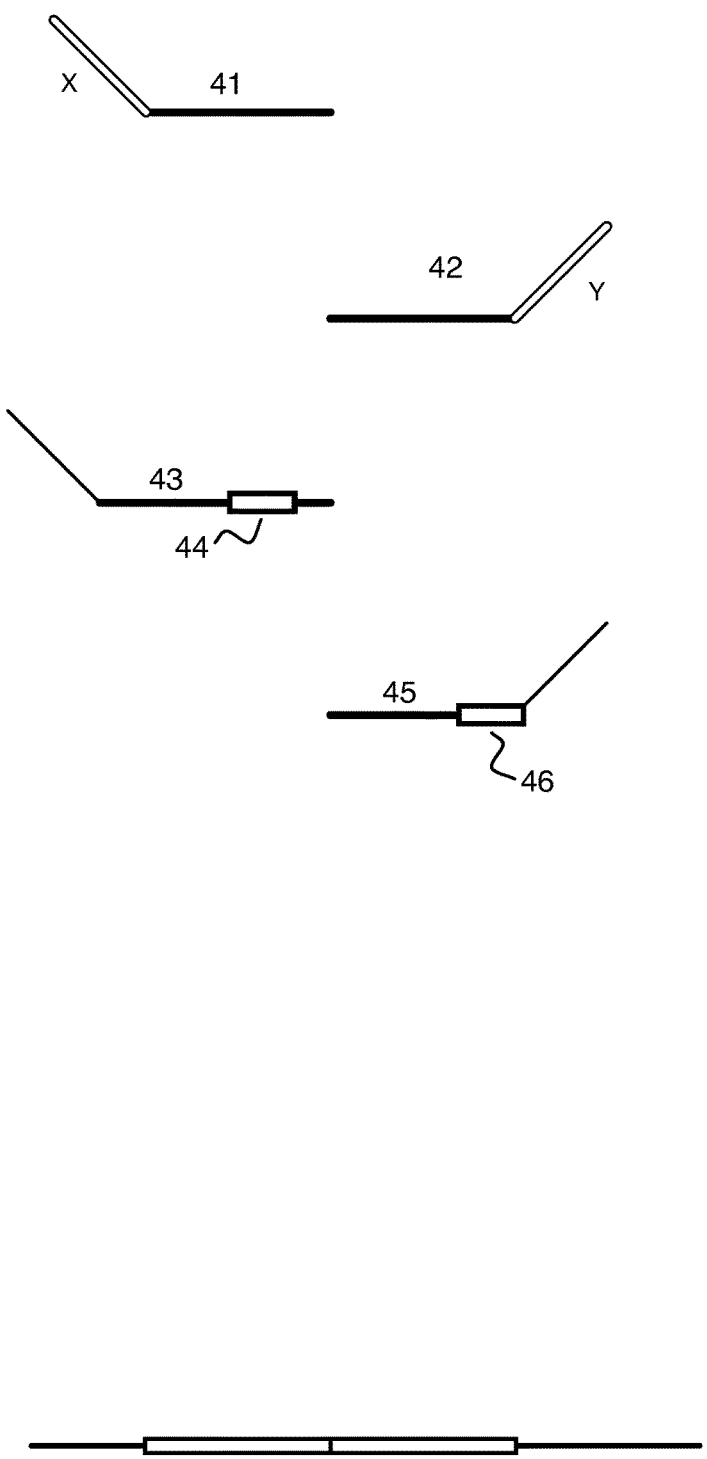
FIG. 4 depicts various oligonucleotides that attenuate primarily during amplification.

An example of such an attenuator has a full-length DR' or UR', but lacks any sequence that can serve as a primer sequence for the primers being used during the amplification step. In FIG. 4, the upstream attenuator 41 has a 5' tail (X) that is different from the P1 sequence that would enable amplification by a P1 primer. Similarly, downstream attenuator 42 has a non-amplifiable sequence (Y) as a 3' tail that is different from sequence P2'. Where it is desirable for the tails of attenuators to have a complete P1 or P2' sequence, the tails can be extended to incorporate a reverse complementary sequence, forming a hairpin loop, to reduce the amplification of ligation products. In other cases, a self-cleaving ribozyme sequence can be incorporated into an attenuator tail to render the ligation product unamplifiable.

Attenuators for reduced amplifiability 43 and 45 incorporate a chemically modified segment (44, 46) that, while allowing ligation to a detector or a second attenuator, is more difficult to amplify than the ligation product of two wildtype detectors. The selection of the modification will depend on the particular polymerase being used in the amplification step. For example, Pfu polymerase stalls when a DNA template contains deoxyUridine (dU) or 2'-deoxyInosine. Another example is a segment that has a 1',2'-dideoxyribose sugar, resulting in an abasic site. Other segments can include a modified nucleotide such as dideoxy nucleotides, deoxyUridine (dU), 5-methylCytosine (5mC), 5-hydroxymethylCytosine (5hmC), 5-formylCytosine (5fC), and 5-carboxylCytosine (5caC), and Inosine. Yet other segments can have nucleotides having modified bases such as 2,6-diaminopurine, 2-aminopurine, 2-fluro bases, 5-bromoUracil, or 5-nitroindole.

Other nonamplifiable attenuators include oligonucleotides having a sugar-phosphate backbone that has a 3'-3' or 5'-5' linkage inversion or a peptide nucleic acid (PNA) backbone.

Another embodiment of useful attenuators contains one or modifications that can be cleaved by treatment after the ligation or optional amplification step. For example, an attenuator can have a dU located so that it will not interfere with hybridization or ligation steps. After ligation, however, products incorporating the dU attenuator can then be cleaved by dU-specific enzymes, such as uracil-DNA glycosylase followed by endonuclease VIII. The cleavage products are thereby rendered unsuitable for amplification or for detection steps that rely on full-length ligation products. An attenuator particularly vulnerable to degradation is a oligonucleotide that contains one or more RNA nucleotides: the resulting ligation product is susceptible to the presence of high pH or $Mg^{++}$ ions, which can occur during amplification reactions such as PCR, effectively preventing RNA-containing ligation products from providing a useful measurement of a target sequence in an assay.

Another approach is to incorporate into an attenuator a selectively cleavable site so that the attenuator can be cleaved without affecting the other components of the assay. For attenuators 43 and 45, such a site can be placed at 44 or 46, for example. A selectively cleavable site can be a restriction enzyme cleavage site that is not present in the wildtype detectors or in the target sequences of interest to be detected. Treatment with the restriction enzyme selectively cleaves the attenuator so that it does not form a detectable product. If an amplification step is used, the restriction treatment can be performed before amplification to reduce amplification of HAT-derived ligation products, or after amplification to cleave HAT-derived amplification products. If sequencing is used as a detection method, the result of the restriction treatment is a reduction in the number of sequenceable products arising from the HAT.

The various features described above can be implemented in a single attenuator, for example an oligonucleotide that has both a block to prevent ligation and a tail that will not be amplified. When attenuators are used in pairs for a target sequence, they can have different features, such as a downstream attenuator with two mutated nucleotides, and a downstream attenuator with a tail that forms a hairpin loop.

Attenuators can also be used at more than one step of the method. For example, if greater attenuation of a particular HAT is desired, more than one attenuator can be provided, such as two or more tailless versions of attenuators 21-25 in a single hybridization reaction. In addition, oligonucleotides can be spiked into the hybridization or amplification steps, where the oligonucleotides contain DR or UR, or subsequences thereof, to compete with the DR and UR target sequences present in the sample.

If it is desired to attenuate three HATs of a sample independently, it may be desirable to attenuate a first target sequence at the hybridization step, attenuate a second target sequence at the ligation step, and attenuate a third target sequence at the amplification step, controlling the degree of attenuation at each step.

If even further attenuation of detectable HAT products is desired, the sample can be pre-treated to remove HAT target sequences prior to step (a), for example by using immobilizable beads or other solid phase that contain oligonucleotides that are specifically complementary to the HAT target sequences. Beads to remove rRNA and globin sequences are commercially available. If a capture sequence on a solid phase surface hybridizes to the UR and/or DR, or a portion of either, then including the capture sequence with the DD and UD at a predetermined ratio can deplete a portion of the HAT. Similarly, an oligo that targets the UR and/or DR or a portion of one or both—and that in turn can be captured onto a surface through a second sequence—can be used to compete with the DD and/or UD. Then, the HAT—to which the competitive, capturable oligonucleotide is hybridized—can be removed from the sample. One skilled in the art will see that there are many combinations that can be used for selective capture and depletion of HATs in a sample.

The selection of the attenuators used in an experiment will depend on the degree of attenuation desired for the particular HAT in a sample. If the target sequences are to be detected after ligation, the desired result will be a decreased number of HAT-related ligation products to be detected. If an amplification step is included, the attenuation can result in fewer HAT-related amplification products to be generated and detected. The net result is to optimize the utilization of assay and detection resources among HATs and the other target sequences of interest. The use of attenuators is particularly effective when the relative number of amplification products for other target sequences of interest is maintained, and preferably enhanced, as demonstrated in Example 3.

The attenuators of the invention can provide attenuation of detected HAT products in a range of any combination of upper and lower limits of 20%, 30%, 40%, 50%, 55%, 60%, 65%, 70%, 75%, 80%, 85%, 90%, 95%, 97%, 98%, 99%, 99.5%, 99.7%, 99.9%, 99.95%, or 99.99% or more, compared to products detected by wildtype HAT detectors.

This invention also provides sets of attenuator oligonucleotides described above. The set can be specific for a sample type, such as a cell or tissue type, that has a plurality of HATs. This invention further provides kits containing the attenuators. The kits and methods of the invention can include attenuators in a range of any combination of upper and lower limits of 1, 2, 5, 10, 20, 50, 100, 200, 500, 1000, 2000, 5000, 10,000, or more HATs. In another aspect, the number of HATs for which attenuators are provided can be in a range of any combination of upper and lower limits of 0.01%, 0.02%, 0.05%, 0.1%, 0.2%, 0.5%, 1%, 2%, 5%, 10%, 20%, 25%, 30%, 35%, 40%, 50%, 60%, or more of the total number of target sequences for a sample.

The kits can be provided with detectors for target sequences of interest. The kits can also have eluent solutions suitable for removing oligonucleotides, such as ligated oligonucleotides, from a tissue sample for further analysis. The kits can further have amplification primers suitable for use with the detectors of the kit.

EXAMPLES

Example 1: Representative Ligation Assay

A representative method is provided to illustrate ligation assays without the attenuators of the invention. Here, over 100 RNA expression products were detected in a sample of cells using a multiplex assay format. For each expression product, the assay was designed to detect one or more sequences of interest within the full sequence of the product. For example, in human cells, a GAPDH gene encodes the enzyme glyceraldehyde 3-phosphate dehydrogenase; three different sequences of interest within the RNA transcript of the GAPDH gene were independently detected. One such RNA sequence, identified here as GAPDH_2, was (SEQ ID NO: 1)
5'-CGACCACUUUGUCAAGCUCAUUUCCUGGUAUGACAACGAAUUUGGC
UACA-3' where a 5' end was designated "upstream" (underlined) and the 3' end was designated "downstream" for the direction of transcription and translation. The same GAPDH_2 sequence can be shown in the 3'-to-5' direction for later convenience of discussion:

(SEQ ID NO: 1)
3'-ACAUCGGUUUAAGCAACAGUAUGGUCCUUUACUCGAACUGUUUCAC
CAGC-5'

A downstream region (DR) was defined as the downstream 25 bases of GAPDH_2:

(SEQ ID NO: 2)
3'-ACAUCGGUUUAAGCAACAGUAUGGU-5' which has a complementary DNA sequence of DR':

(SEQ ID NO: 3)
5'-TGTAGCCAAATTCGTTGTCATACCA-3'

The upstream region (UR) was defined as the upstream 25 bases of GAPDH_2:

(SEQ ID NO: 4)
3'-CCUUUACUCGAACUGUUUCACCAGC-5' which has a complementary DNA sequence of UR':

(SEQ ID NO: 5)
5'-GGAAATGAGCTTGACAAAGTGGTCG-3'

For GAPDH_2, a pair of detectors was designed: a downstream detector (DD) having the DR' sequence, and an upstream detector (UD) having the UR' sequence. Similar pairs were designed for each of the target sequences of interest to provide a pool of detectors for the assay. In this example, all the upstream detectors were phosphorylated at the 5' end.

In this particular example, an amplification step was to be performed later in the experiment using two primers, P1 and P2, so all UDs in the experiment included a primer sequence (P1) and all URs included a complementary primer sequence (P2'). Because amplification is not necessary to the practice of the invention, however, the sequence of the specific primers and primer sequences is a matter of selection to suit the particular amplification method, if used.

At least 10 ng of RNA isolated from human kidney or liver cell lines was placed in a well of a microtiter plate for each assay experiment. To each well was added 20 μL of 2X Binding Cocktail, which contained 5 nM of each detector (providing a final input of 0.1 pmoles per oligo), 100 nM biotinylated oligo$(dT)_{25}$ (SEQ ID NO: 13), and 5 μL streptavidin-coated magnetic beads in a Wash Buffer (40 mM Tris-Cl pH 7.6, 1 M NaCl, 2 mM EDTA disodium, 0.2% SDS).

The plate was heated for 10 min at 65° C. to denature the RNA, then the temperature was ramped down over 40 min to 45° C. to allow the detectors to anneal to the RNA sample.

The plate was then transferred to a magnetic base to immobilize the beads, allowing the supernatant, containing unbound and excess detectors, to be aspirated from the wells. The beads were washed at least three times with 50 µL Wash Buffer.

To each well was added 5 Weiss units of T4 DNA ligase in 20 µL of 1× ligation buffer, as provided by the supplier. After the beads were resuspended by pipette, the plates were incubated for 60 min at 37° C. to allow template-dependent ligation of DDs to UDs as appropriate. After the ligation reaction, the beads were immobilized and washed twice with 50 µL Wash Buffer. To release the ligated detectors from their RNA targets, the beads were resuspended in 30 µL and incubated for 5 min at 65° C. After incubation, the beads were immobilized, and the supernatant was removed and transferred to a storage plate.

For the optional amplification step, 5 µL of the supernatant, containing the ligation products, was transferred to a well of a PCR plate. Then 10 µL of a PCR cocktail was added, containing 0.45 U Taq polymerase, 0.6 µM P1 primer, 0.6 µM P2 primer, 1.5 mM MgCl$_2$, and 200 µM dNTPs. The thermocycler used the following program: 10 min at 94° C., followed by 20 to 25 cycles of 30 sec at 94° C., 30 sec at 58° C., and 30 sec at 72° C. The amplification products were then sequenced according to manufacturer's instructions. This representative ligation assay can be modified by the attenuators of the invention as in the following examples.

Example 2: Mutated Sequence Attenuators

In this experiment, the DD and/or UD were replaced with various attenuator oligos having one, two, or three mismatched bases. As discussed in Example 1, the DR' of the DD for GAPDH_2 had the sequence 5'-TGTAGCCAAAT-TCGTTGTCATACCA-3' (SEQ ID NO: 3), so that the three nucleotides at the 3' terminus can be represented as -CCA-3'. The full sequence can be designated as the wildtype DD. Mutated versions of the DD were prepared, each having 3'-terminal sequences as follows (mutated bases shown in bolded lowercase):

| downstream attenuator | 3'-terminus | mutated positions |
|---|---|---|
| wildtype DD | -CCA | 0 |
| GAPDH_MM3_0b_D | -CCt | 1 |
| GAPDH_MM3_1b_D | -CgA | 1 |
| GAPDH_MM3_2b_D | -gCA | 1 |
| GAPDH_MM3_3b_D | -gCt | 2 |
| GAPDH_MM3_5b_D | -ggA | 2 |
| GAPDH_MM3_6b_D | -Cgt | 2 |
| GAPDH_MM3_4b_D | -ggt | 3 |

Similarly, the UR' of the UD had the sequence (SEQ ID NO: 5)
5'-GGAAATGAGCTTGACAAAGTGGTCG-3', which can be designated as the wildtype UD, with a 5'-terminal sequence of /5Phos/GGA-. In this example, the sequence derived from the upstream regions remains underlined. Attenuator versions of the UD were prepared, each having 5'-terminal sequences:

| upstream attenuator | 5'-terminus | mutated positions |
|---|---|---|
| wildtype UD | /5Phos/GGA- | 0 |
| GAPDH_MM3_0b_U | /5Phos/cGA- | 1 |
| GAPDH_MM3_1b_U | /5Phos/GcA- | 1 |
| GAPDH_MM3_2b_U | /5Phos/GGt- | 1 |
| GAPDH_MM3_3b_U | /5Phos/cGt- | 2 |
| GAPDH_MM3_5b_U | /5Phos/Gct- | 2 |
| GAPDH_MM3_6b_U | /5Phos/ccA- | 2 |
| GAPDH_MM3_4b_U | /5Phos/cct- | 3 |

Combinations of the 8 DDs (wildtype and 7 mutated sequences) and 8 UDs (wildtype and 7 mutated sequences) were tested for attenuation of ligation in 64 experiments on RNA isolated from human kidney cell lines. As shown in FIG. 5, the positive control, using the wildtype DD and wildtype UD, correctly detected the presence of GAPDH_2 in the sample RNA by generating a species that joined DR' to UR', and specifically containing the following internal sequence at the ligation junction:

(SEQ ID NO: 6)
5'-CCAGGA-3'

In each of the experiments, a DD and an UD were provided for a ligation experiment, and the ligation products were analyzed by sequencing and counting the number of reads containing DR' joined to UR', except with one of the 64 possible internal sequences formed by the junction. For example in one experiment, the ligation reaction was provided with downstream attenuator GAPDH_MM3_2b_D (or "2b_D") serving as the downstream detector for GAPDH_2, and upstream attenuator GAPDH_MM3_2b_U ("2b_U") serving as the upstream detector for GAPDH_2. In the presence of GAPDH_2 sequence in the RNA sample, the pair of upstream and downstream attenuators generated a certain number of ligation products having the internal sequence (SEQ ID NO: 7)
5'-gCAGGt-3'.

The formation of these ligation products was sufficient to correctly detect the presence of GAPDH_2 in the samples, but at an attenuated level (33%) compared to the comparable experiment using wildtype detectors.

Greater attenuation was observed when using pairs of attenuators having more than one mutation. For example, the pairing of 5b_D and 3b_U yielded ligation products with the internal sequence (SEQ ID NO: 8)
5'-ggAcGt-3' which resulted in detection of GAPDH_2, but at a much reduced level of only 0.58% of the positive control, representing an attenuation of 99.42%. No ligation products were detected when using the pair of 4b_U and 4b_U, with three mutations at each terminus. As disclosed herein, the degree of attenuation is not easily correlated with the number or position of mismatches. For example, the pairing of 0b_D and 0b_U yielded an attenuated level of 7.3%, which was ten-fold higher than most other combinations with similar attenuators. Nevertheless, when attenuation of a HAT such as GAPDH_2 is desired, the use of mismatched attenuators provides authentic detection of HATs without generating undesirable numbers of ligation product.

Example 3: Bridge Attenuators

Ligation assays were performed where a bridge attenuator was added to a ligation reaction, in addition to the wildtype DD and wildtype UD, at a pre-determined ratio of concentration of attenuator to concentration of wildtype DD and wildtype UD. The sample was RNA from a human kidney cell line. An attenuator specific for the DR and UR of GAPDH_2 was prepared:

(SEQ ID NO: 9)
5'-TGTAGCCAAATTCGTTGTCATACCAGGAAATGAGCTTGACAAAGTG
GTCG-3' and included in a pool of 9 bridge attenuators for various attenuation targets. The attenuator pool was added in varying concentrations to eight separate reactions, each containing pairs of UD and DD oligos to detect 443 target sequences, among them GAPDH_2, while the concentration of UD and DD were kept constant. The result for ligation products indicating the presence of GAPDH_2 are shown:

| concentration of added bridge attenuator (relative to UD) | average number of reads | relative to positive control |
|---|---|---|
| no bridge added | 4478 | (100.0%) |
| +1X bridge | 2438 | 54.4% |
| +3X bridge | 1429 | 31.9% |
| +10X bridge | 602 | 13.5% |

As shown, inclusion of bridge attenuators reduces the number of products detected for target sequence GAPDH_2 in a dose-dependent fashion. Moreover, FIG. 6 shows that for selected target sequences, adding the bridge attenuators for GAPDH_2 allowed the lower-abundance target sequences to be detected at higher, but representative levels.

Skilled artisans will appreciate that additional embodiments are within the scope of the invention. The invention is defined only by the following claims, and limitations from the specification or its examples should not be imported into the claims.

We claim:

1. A method for detecting a plurality of target nucleic acid sequences of interest in a sample, wherein each target sequence has an upstream region (UR) and a downstream region (DR), the method comprising:
   (a) contacting the sample with a pool of detector oligos comprising, for each target sequence,
      (1) a downstream detector oligo (DD) comprising a portion complementary to the downstream region of the target sequence (DR'), and
      (2) an upstream detector oligo (UD) comprising a portion complementary to the upstream region of the target sequence (UR'),
      wherein, for a predetermined set of potentially high abundance target sequences (HATs) in the sample, also contacting the sample with
      (3) an attenuator oligonucleotide that comprises a portion at least partially complementary to one of the downstream or upstream regions of a HAT, and further comprises a nonextendable or nonligatable blocking group, or a nonamplifiable segment; and
   (b) ligating a downstream detector oligo for a target sequence to a corresponding upstream detector oligo if both are hybridized to the downstream and upstream regions of a target sequence in the sample;
   thereby attenuating the number of HAT products to be detected.

2. The method of claim 1, wherein the sample is provided on a solid substrate.

3. The method of claim 1, wherein the sample is formalin-fixed paraffin-embedded (FFPE) tissue or cells.

4. The method of claim 1, wherein at least one of the detector oligos is detectably labeled.

5. The method of claim 1, wherein at least one of the detector oligos has a barcode sequence.

6. The method of claim 1, wherein steps (a) and (b) are performed on the sample in situ.

7. The method of claim 1, wherein after step (b), the ligated oligos are eluted from the sample and collected.

8. The method of claim 1, further comprising the step of
   (c) amplifying the ligated oligos.

9. The method of claim 8, wherein the attenuator further comprises an amplification sequence.

10. The method of claim 9, wherein the amplified products incorporate a barcode sequence that is specific to the sample.

11. The method of claim 8, further comprising:
    (d) detecting the amplified products by sequencing.

12. The method of claim 8, further comprising:
    (d) detecting the amplified products, whereby a lower abundance target sequence is detected at a higher level.

13. The method of claim 1, further comprising
    (d) detecting the ligated products by sequencing.

14. The method of claim 1, wherein the set of HATs contains a sequence partially encoding a product selected from the group consisting of myoglobins, actins, tubulins, ubiquitins, heat-shock proteins (HSPs), ribosomal proteins, ribosomal RNAs (rRNAs), micro-RNAs (miRNAs), and small nuclear RNAs (snRNAs).

15. The method of claim 1, wherein the set of HATs contains a sequence partially encoding a product selected from the group consisting of cytochrome c, glyceraldehyde 3-phosphate dehydrogenase (GAPDH), ribosomal protein L7 (RPL7), ribosomal protein S6 (rpS6), snRNA RNUs, phosphoglycerokinase (PGK), tyrosine 3-monooxygenase/tryptophan 5-monooxygenase activation protein zeta (YWHAZ), beta-actin, and beta-tubulin.

16. The method of claim 1, wherein the set of HATs contains a sequence partially encoding a product selected from the group consisting of alpha-2-microglobulin, vimentin, and fibronectins.

17. The method of claim 1, wherein a HAT is a sequence partially encoding a cytochrome selected from the group consisting of mitochondrially encoded cytochrome b (MT-CYB), outer mitochondrial membrane cytochrome b5 type B, microsomal cytochrome b5 type A (ACYB5A), and ascorbate-dependent cytochrome b3 (CYBASC3).

18. The method of claim 1, wherein an attenuator further has a portion that is complementary to a region adjacent to the downstream or upstream region of a HAT.

19. The method of claim 18, wherein the downstream and upstream regions of the HAT are separated by one or more nucleotides, and the attenuator has a portion that is complementary to the one or more nucleotides.

20. The method of claim 1, wherein an attenuator has a portion that is complementary to at least a portion of the downstream region of a HAT and another portion that is complementary to at least a portion of the upstream region of the HAT.

21. The method of claim 20, wherein the attenuator hybridizes by circularization.

22. The method of claim 1, wherein the attenuator has at least one mismatched base relative to the DR or UR of the HAT.

23. The method of claim 22, wherein the attenuator has a portion partially complementary to a downstream region of a HAT, and has 1, 2, or 3 mismatched bases at any of the positions at the 3' end or at 1 or 2 positions from the 3' end.

24. The method of claim 22, wherein the attenuator has a portion partially complementary to an upstream region of a HAT, and has 1, 2, or 3 mismatched bases at any of the positions at the 5' end or at 1 or 2 positions from the 5' end.

25. The method of claim 1, wherein the blocking group is selected from the group comprising 2',3'-dideoxynucleotide, 3'-propyl spacer, 3'-dehydroxylation, and 3'-amination.

26. The method of claim 1, wherein the blocking group is a nonhybridizing portion.

27. The method of claim 26, wherein the nonhybridizing portion of an attenuator forms a hairpin loop.

28. The method of claim 1, wherein the attenuator has a selectively cleavable site.

29. The method of claim 1, wherein the attenuator oligonucleotide comprises a portion at least partially complementary to one of the downstream or upstream regions of a HAT, and further comprising a portion at least partially complementary to the other region of the HAT.

30. The method of claim 1, wherein the attenuator oligonucleotide comprises a nonextendable blocking group.

31. The method of claim 1, wherein the attenuator oligonucleotide comprises a nonligatable blocking group.

32. The method of claim 1, wherein the attenuator oligonucleotide comprises a nonamplifiable segment.

33. The method of claim 32, wherein the nonamplifiable segment comprises a reverse complementary sequence.

34. The method of claim 32, wherein the nonamplifiable segment comprises a nonamplifiable tail.

35. The method of claim 32, wherein the nonamplifiable segment is RNA.

36. The method of claim 1, wherein the sample is provided in liquid phase.

37. The method of claim 1, further comprising
(d) detecting the ligated products, whereby detection of a lower abundance target sequence is detected at a higher level.

* * * * *

SEQUENCE LISTING

<160> NUMBER OF SEQ ID NOS: 13

<210> SEQ ID NO 1
<211> LENGTH: 50
<212> TYPE: RNA
<213> ORGANISM: Homo sapiens

<400> SEQUENCE: 1
cgaccacuuu gucaagcuca uuuccuggua ugacaacgaa uuuggcuaca        50

<210> SEQ ID NO 2
<211> LENGTH: 25
<212> TYPE: RNA
<213> ORGANISM: Homo sapiens

<400> SEQUENCE: 2
ugguaugaca acgaauuugg cuaca        25

<210> SEQ ID NO 3
<211> LENGTH: 25
<212> TYPE: DNA
<213> ORGANISM: Homo sapiens

<400> SEQUENCE: 3
tgtagccaaa ttcgttgtca tacca        25

<210> SEQ ID NO 4
<211> LENGTH: 25
<212> TYPE: RNA
<213> ORGANISM: Homo sapiens

<400> SEQUENCE: 4
cgaccacuuu gucaagcuca uuucc        25

<210> SEQ ID NO 5
<211> LENGTH: 25

-continued

```
<212> TYPE: DNA
<213> ORGANISM: Homo sapiens

<400> SEQUENCE: 5
ggaaatgagc ttgacaaagt ggtcg                                           25

<210> SEQ ID NO 6
<211> LENGTH: 6
<212> TYPE: DNA
<213> ORGANISM: Homo sapiens

<400> SEQUENCE: 6 ccagga                                                                 6

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      junction sequence formed by ligation of mutated oligos

<400> SEQUENCE: 7 gcaggt                                                                 6

<210> SEQ ID NO 8
<211> LENGTH: 6
<212> TYPE: DNA
<213> ORGANISM: Artificial Sequence
<220> FEATURE:
<223> OTHER INFORMATION: Description of Artificial Sequence: Synthetic
      junction sequence formed by ligation of mutated oligos

<400> SEQUENCE: 8 ggacgt                                                                 6

<210> SEQ ID NO 9
<211> LENGTH: 50
<212> TYPE: DNA
<213> ORGANISM: Homo sapiens

<400> SEQUENCE: 9
tgtagccaaa ttcgttgtca taccaggaaa tgagcttgac aaagtggtcg                50

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      P1 downstream amplification sequence or primer

<400> SEQUENCE: 10
caagcagaag acggcatacg ag                                              22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      P2' upstream amplification sequence

<400> SEQUENCE: 11
atctcggtgg tcgccgtatc att                                             23
```

```
<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      P2 amplification primer

<400> SEQUENCE: 12
aatgatacgg cgaccaccga gat                                            23

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttttttttt tttttttttt ttttt                                          25
```